United States Patent [19]

Dudley, deceased et al.

[11] 4,302,368

[45] * Nov. 24, 1981

[54] NONTHROMBOGENIC ARTICLES AND METHOD OF PREPARATION

[75] Inventors: Betty J. Dudley, deceased, late of Durham, N.C., by Kenneth H. Dudley, executor; Joel L. Williams, Cary, N.C.

[73] Assignee: Becton, Dickinson and Company, Paramus, N.J.

[*] Notice: The portion of the term of this patent subsequent to Sep. 26, 1995, has been disclaimed.

[21] Appl. No.: 76,201

[22] Filed: Sep. 17, 1979

Related U.S. Application Data

[63] Continuation-in-part of Ser. No. 899,343, Apr. 24, 1978, abandoned, which is a continuation of Ser. No. 752,247, Dec. 20, 1976, abandoned, and a continuation-in-part of Ser. No. 888,951, Mar. 22, 1978, abandoned, which is a continuation of Ser. No. 764,474, Jan. 31, 1977, Pat. No. 4,116,898.

[51] Int. Cl.$^3$ ............................................. C08L 5/10
[52] U.S. Cl. ................................. 260/17.4 R; 3/1; 260/9; 424/83
[58] Field of Search .............. 260/9, 17.4 R; 424/78, 424/82, 83, 183; 428/447, 422, 522, 523

[56] References Cited

U.S. PATENT DOCUMENTS

| | | | |
|---|---|---|---|
| 3,457,098 | 7/1969 | Leininger | 424/183 |
| 3,514,438 | 5/1970 | Bixler | 3/1 |
| 3,616,935 | 11/1971 | Love | 424/183 |
| 3,617,344 | 11/1971 | Leininger | 428/422 |
| 3,634,123 | 1/1972 | Eriksson | 428/447 |
| 3,755,218 | 8/1973 | Yen | 260/9 |
| 3,810,781 | 5/1974 | Eriksson | 424/183 |
| 3,844,989 | 10/1974 | Harumiya | 260/17.4 R |
| 3,846,353 | 11/1974 | Grotta | 260/9 |
| 4,118,485 | 10/1978 | Eriksson | 424/183 |

*Primary Examiner*—Paul R. Michl

[57] ABSTRACT

The disclosure is of articles having reduced thrombogenicity and which are useful for purposes requiring their contact with whole blood. The articles comprise solid, polymeric resin substrates to which there is fixed a compound of the formula:

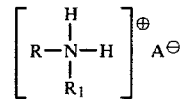

wherein R is alkyl of 12 to 18 carbon atoms, inclusive, $R_1$ is lower alkyl and A is the negative ion of a soluble salt of heparin. The articles advantageously exhibit low toxicity and excellent blood compatibility when used for purposes which bring them into contact with whole blood for prolonged periods of time.

9 Claims, 4 Drawing Figures

NONTHROMBOGENIC ARTICLES AND METHOD OF PREPARATION

CROSS-REFERENCE TO RELATED APPLICATIONS

This application is a continuation-in-part of U.S. patent application Ser. No. 899,343 filed Apr. 24, 1978 now abandoned and which was a continuation of U.S. patent application Ser. No. 752,247 filed Dec. 20, 1976, now abandoned and also a continuation-in-part of U.S. patent application Ser. No. 888,951 filed Mar. 22, 1978 now abandoned and which was a continuation of U.S. patent application Ser. No. 764,474 filed Jan. 31, 1977, now U.S. Pat. No. 4,116,898.

BACKGROUND OF THE INVENTION

1. Field of the Invention

The invention relates to non-thrombogenic articles and to methods of reducing thrombogenically associated with polymer resin articles.

2. Brief Description of the Prior Art

Representative of the prior art are the disclosures of U.S. Pat. Nos. 3,457,098; 3,634,123; 3,810,781; 3,846,353; and 4,118,485. As succinctly stated in U.S. Pat. No. 3,846,353, "It has been known for many years that a basic problem in the development of prostheses for intravascular replacement lies with the complicated processes occurring at the bloodgraft interface. The addition of a solid foreign material to the blood stream results in clot formation on that material. This interface activity occurs no matter what the foreign material might be. Porous prosthetics have proven to be useful in the larger vessel, but have failed when adapted to the smaller artery. Certain non-porous materials have been used but also have demonstrated various disadvantages. Solid or imperforate materials are preferred in the field of artificial internal organ development. Pumping chambers, arteries and materials for encompassing structures having moving parts would demand the property of elasticity as its constituent, prompting an additional requirement of the ideal vascular prosthetic material. It would also be advantageous if that same material could be varied in its elastic properties to the point of rigidity.

Naturally, polymers, both natural and synthetic and particularly certain synthetic plastics have come to the fore as preferred materials for those prosthetics. Their major drawback, however, is their thrombogenicity. Even though plastics are used in various apparatus such as heart-lung machines, kidney machines, and artificial heart valves and patches, the tendency of these materials to cause coagulation necessitates the use of anticoagulants such as heparin. Even such plastics as Teflon (polytetrafluoroethylene) and the silicone rubbers which are more compatible with blood than most plastics, still show thrombogenic characteristics. The first real advance in the preparation of nonthrombogenic materials was described by Dr. Vincent Gott. The method used by Dr. Gott comprised treating a graphited surface first with Zephiran (benzalkonium chloride) and then with heparin. Materials treated in this way were nonthrombogenic in vivo for long periods of time. The major disadvantage, however, with these materials, was that the method could only be practiced on rigid plastics and a need still exists for a suitable flexible nonthrombogenic plastic, as well as a method of producing the same.

Various methods have been devised for producing such a material, most of which involve chemically bonding a quaternary ammonium salt to the polymer and then heparinizing the same. Usually, this is done by incorporating an amine in the polymer, quaternizing the amine, and then heparinizing the quaternized material. The disadvantages associated with these methods are numerous. The materials prepared by these methods have usually been satisfactory on a small laboratory scale, but could not easily be scaled up to a practical method. Furthermore, these methods were quite satisfactory for preparation and evaluation of individual polymers, the techniques varying from polymer to polymer. A major drawback, based on these differences in techniques, is that heparinization of a composite structure containing more than one type of polymer could not be easily done. Moreover, many of the techniques involve several steps requiring a variety of reagents, solvents, and reaction conditions."

Many of the disadvantages and drawbacks of the earlier methods for rendering polymeric materials less thrombogenic were removed in the methods described in the above-identified U.S. patent applications. These latter methods comprise:

first absorbing on the surface of the material, a quaternary ammonium salt. The material is then "heparinized" by exposure to a salt of heparin in solution. The heparin is bound to the polymer material through ionic bonds with the surface absorbed quaternary ammonium salt. The treated polymeric materials exhibit an advantageous reduction in thrombogenicity as reflected by extended periods of time during which the materials may be in contact with blood without inducing thrombosis. In addition, it has been observed that the quaternary ammonium salt-heparin complex treated materials of the prior art have a degree of toxicity toward the blood or the host animal in which the treated polymer is implanted. It is believed that the toxicity is generated by leaching of the quaternary compound from the polymer substrate over a period of time.

By the method of our invention, relatively stable articles for use in association with whole blood are obtained, which exhibit unexpectedly low toxicity and unexpectedly reduced thrombogenecity as reflected by unusually long periods of time during which they may be in contact with blood without inducing a thrombosis. By the method of the invention, preformed articles, i.e.; valves, pins, containers, tubing and the like, may be treated to reduce thrombogenicity without increasing toxicity and without altering the geometry, configuration and/or dimensions of the article. This also obviates the need for post-forming the article as often necessitated in prior art treatments by shrinking or swelling or deterioration of the treated article.

SUMMARY OF THE INVENTION

The invention comprises an article for use in association with whole blood, which comprises;

a solid, polymeric resin substrate; and a compound of the formula:

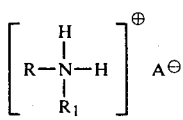
(I)

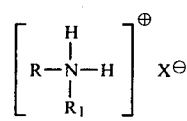
(II)

wherein R is alkyl of 12 to 18 carbon atoms, inclusive, $R_1$ is lower alkyl and A represents the negative ion of a salt of heparin, affixed to the substrate. The moiety A is in fact the active heparin moiety, i.e.; the negative ion of heparin having attached sulfate and sulfonate groups. The moiety A is supplied by salts of heparin such as sodium heparin, lithium heparin, potassium heparin, calcium heparin and the like.

The term "lower alkyl" as used herein means alkyl of 1 to 6 carbon atoms inclusive such as methyl, ethyl propyl, butyl heptyl, hexyl and isomeric forms thereof.

The invention also comprises a method for making the articles of the invention.

DETAILED DESCRIPTION OF THE INVENTION

The solid, polymeric resin materials advantageously treated by the method of the invention and used to fabricate articles of the invention may be any polymeric resin, natural or synthetic, conventionally employed to fabricate articles commonly employed in contact with blood. For example, catheters, artificial blood vessels, valves and like prosthetics are frequently fabricated from polyethylene, polyacrylics, polypropylene, polyvinyl chloride, polyamides, polyurethanes, polyvinylpyrrolidone, polyvinyl alcohols, cellulose acetate, polystyrene, polytetrafluoroethylene, polyesters such as polyethylene terephthalate, silicone rubber, natural rubber, polycarbonates and like polymeric resins and hydrogels, thereof. Such polymeric resins may be treated by the method of the invention and may be employed as the polymeric resin substrate for the articles of the present invention. The resin substrate may be rigid or flexible in character, cellular or non-cellular, porous or non-porous. Also within the scope of the invention are metal or ceramic materials coated with polymer resins such as described above.

The polymeric resin substrate may be first formed into any desired shape, size or configuration. Representative of such are valves, pins, containers, sleeves, connectors, medical-surgical tubing, prosthetic devices and the like of any size.

In accordance with the method of the invention, to the polymeric resin substrate there is first affixed by absorption on the surface thereof, a quaternary ammonium salt of the general formula:

wherein R and $R_1$ are as defined previously and X represents a negative monovalent ion such as halogen. The term halogen as used herein is embracive of chlorine, bromine, iodine and fluorine.

The Compounds of Formula (II) are affixed to the polymeric resin substrates by their permeating throughout the molecular structure of the resin substrate, i.e.; a chemisorption. It is believed that the $C_{12}$ to $C_{18}$ alkyl chain portion of the compounds of formula (II) may also bind to the polymeric resin substrate. The compounds (II) may be chemisorbed into the polymeric resin substrate by steeping the substrate in a dispersion of the compounds (II) (Steeping may be carried out at ambient or at elevated temperatures up to or slightly above the softening point temperature for the resin substrate). By the term "softening point temperature" we mean the temperature at which the surface of the resin substrate becomes pliable due to the additional mobility of the substrate molecules. Following fixation of the quaternary ammoniun salt compound (II) to the surface of the polymeric resin substrate, the surface with affixed compound (II) is "heparinized" by contact with a solution of a salt of the heparin.

Figure 1:
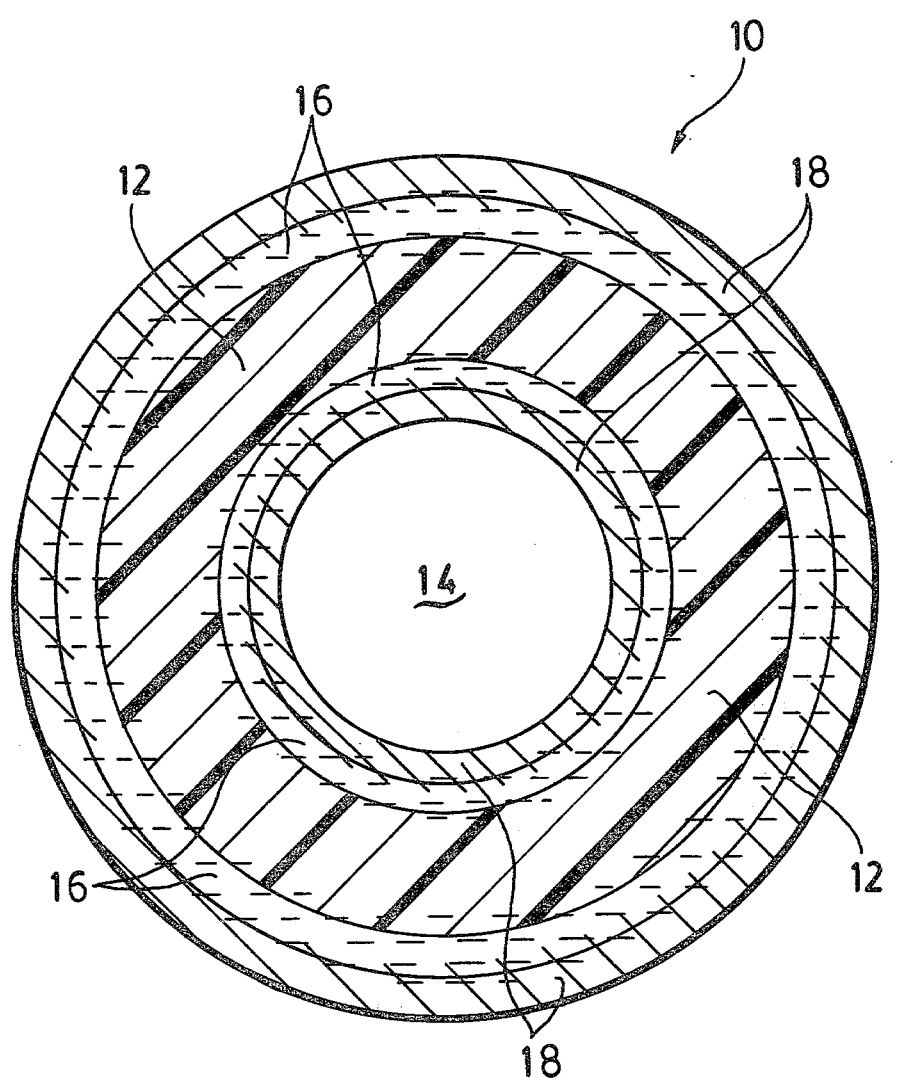
FIG. 1 is a cross-sectional view of an embodiment article (medical-surgical tube) of the invention.

The articles of the invention may be prepared by the method of the invention which as described above first comprises providing a polymeric resin substrate, as previously defined, in the desired article configuration and size. As an example, FIG. 1 of the accompanying drawing shows a cross-section of a medical-surgical tube 10 of the invention. The tube 10 comprises a tube polymer substrate 12 and a lumen 14. The substrate 12 may be steeped for from about 1 to 72 hours in an aqueous dispersion of a compound of the formula (II) given above at a temperature of from room temperature to at or just above the softening point temperature for the substrate resin. The concentration of compound (II) in the aqueous dispersion is not critical, but advantageously is within the range of from about 0.01% to 20% by weight. This assures that a monolayer 16 of relatively high concentration of the compound of formula (II) is provided in contact with the surface of the resin substrate. Preferably the aqueous dispersion is degassed before placing the substrate therein, by heating to a temperature of about 100° C. for 15 minutes. This degassing assures obviation of oxidation of the substrate surface during steeping. Following the period of steeping, the substrate 12 is removed from the dispersion of the compound of formula (II) and allowed to cool to ambient temperatures. The resulting article, upon drying, bears a surface layer 16 as shown in FIG. 1, of the compound of formula (II) on inner and outer surfaces of substrate 12. The layer 16 actually penetrates to some extent the surface of substrate 12, and is chemisorbed or fixed to the substrate 12, as shown in the FIG. 1. The treated substrate may then be washed with water or an organic solvent for the compound (II) to remove excess compound (II) not firmly fixed to the substrate 12.

Subsequent to steeping in the dispersion of compound (II) and washing, the treated substrate 12 with its compound (II) layer 16 is then "heparinized" by immersion in an aqueous solution of a salt of heparin such as sodium heparin. The temperature at which immersion occurs is advantageously within the range of from about room temperature to about 80° C., but preferably less than the softening point temperature for the resin substrate. The length of immersion is dependent on the temperature used, but is generally long enough to permit the substrate 12 to pick up at least about 0.1 International Unit heparin per square centimeter of substrate surface. At a temperature of circa 70° C., for example, this is usually accomplished in about 1 hour, using a heparin solution with a concentration of from about 1% to saturation, i.e.; circa 20% by weight of sodium heparin, preferably from 5% to saturation. During "heparinization" the negative ion of the sodium heparin complexes with the positive ion of the compound of formula (II) according to the scheme:

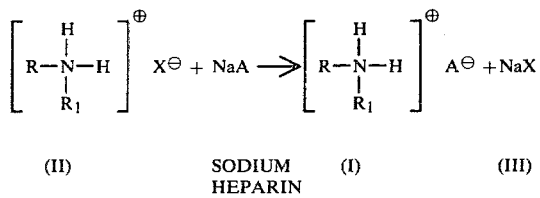

(II)     SODIUM    (I)      (III)
           HEPARIN wherein R, $R_1$, X and A are as previously defined. The product, which advantageously has at least 2.0 μg of heparin moiety per $cm^2$ of surface area attached following "heparinization" is schematically shown in FIG. 1 where the layer 18 covering inner and outer layers 16 represents the active heparin moiety which is complexed with the compound (II) of coating layers 16 and in fact also permeates to some extent the substrate 12. It will be appreciated that although A has been illustrated by the negative ion of sodium heparin in the above schematic formula, it may be provided by any salt compound of heparin. Illustrative of such compounds are lithium heparin, potassium heparin, calcium heparin and the like.

Following the heparinization step, the desired product as schematically exemplified in FIG. 1 may be removed from the heparin solution, allowed to cool, washed with water and/or saline, dried and used in contact with blood. The article so obtained will exhibit reduced thrombogenicity.

The following examples illustrate the method of making and using the invention and represent the best mode contemplated by the inventors of carrying out the invention but are not to be construed as limiting the invention in any way.

Figure 2:
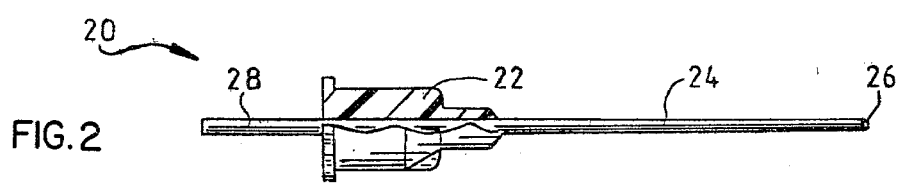
FIG. 2 is a view-in-perspective, cross-sectioned in part to show a cannula which is advantageously employed in test evaluating the method of the invention.

The blood compatibility (clotting times) reported were determined by the test method of our U.S. patent application Ser. No. 899,342 filed Apr. 24, 1978 and which was a continuation of our U.S. patent application Ser. No. 752,247, filed Dec. 20, 1976 and now abandoned. The method may be carried out as described below in conjunction with the FIGS. 2-4 of the accompanying drawings. In the procedure of the test method, it is advantageous to provide a cannula as shown in FIG. 2, a view-in-perspective of a preferred cannula 20 having a hub 22 to facilitate holding the cannula 20, a barrel 24 including a tip 26 and a tubular extension 28. The extension 28 preferably extends distally from hub 22 about 1 cm. Barrel 24 and extension 28 are integral and pass through hub 22 as a unitary, uninterrupted tubular structure as shown in FIG. 2 and are preferably fabricated from a relatively flexible, inert material such as polytetrafluoroethylene. The inner diameter, i.e.; the diameter of the bore traversing cannula 20 is preferably sufficient to receive in a close fit the tubular form of the material to be tested.

Figure 3:
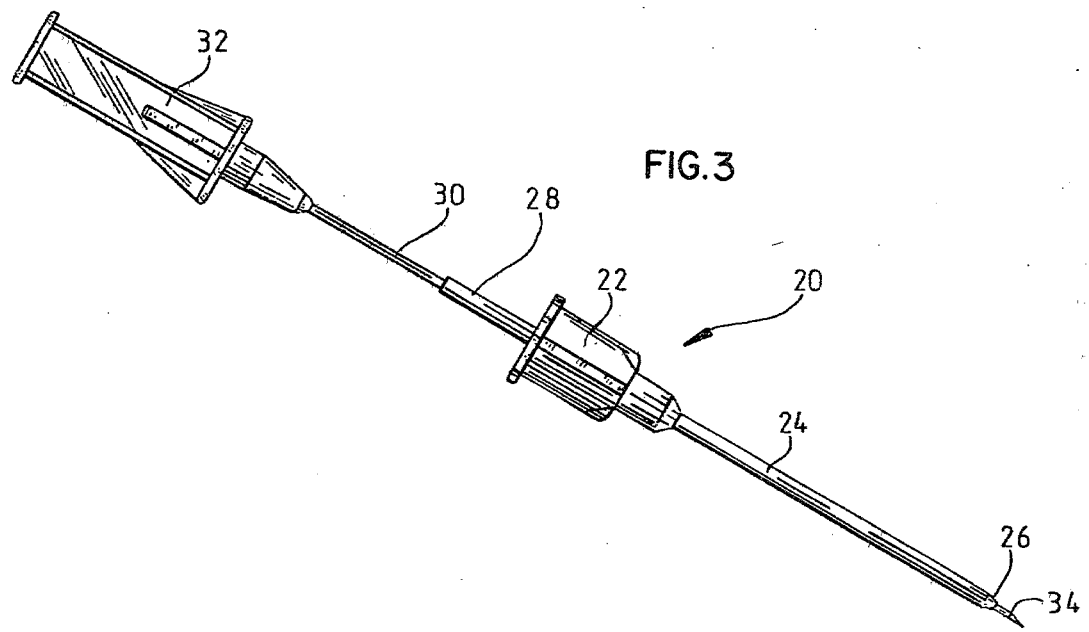
FIG. 3 is an isometric view of the cannula of FIG. 2, showing the insertion of a needle therein for gaining entry into a mamalian vein.
Figure 4:
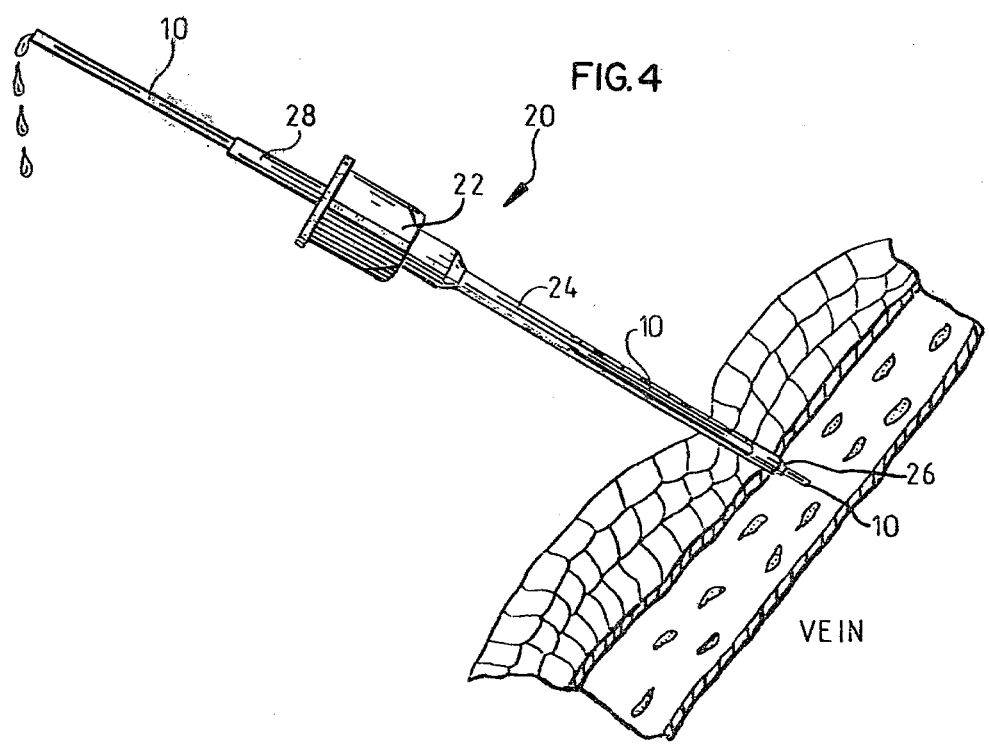
FIG. 4 is a view-in-perspective of a catheter formed of material to be tested for blood compatibility, inserted in a mammalian vein with the assistance of the cannula of FIG. 2, which is shown cross-sectioned-in-part.

To facilitate entry of the cannula 20 into the blood vessel of a mammal, a tubular stylet needle 30 having a hub 32 is inserted into the bore of cannula 20 as shown in the isometric view of FIG. 3. As shown, the shank of needle 30 extends out of cannula tip 26. The needle point 34 is a sharp surgical edge capable of cutting an entry into a blood vessel. The needle 30 may, if desired, include a tight-fitting stylet member (not shown in FIG. 3) removably mounted in its bore to close that bore. The assembly of cannula 20 and needle 30 may be used to gain entry into the blood vessel, such as a vein, of a mammal using conventional blood vessel entry techniques. Following such entry, needle 30 is withdrawn from cannula 20, leaving the latter's tip 26 positioned in the blood vessel. The tube or catheter 10 of material to be tested for its blood compatibility is then inserted through the cannula 20 and into the blood vessel as shown in FIG. 4. Preferably the catheter extends at least 0.5 cm. past the tip 26 so that blood entering the catheter is generally not in contact with cannula 20 before contact with the catheter 10. In each test, canines (beagles, 10 and 12 kilograms in weight) are used to supply the blood required in the test method. The dogs are prepared on the day of use by first anesthetizing them with combuthal or nembutal by inserting the needle of an infusion set into one of the leg veins. When the vein is punctured, the drug is infused into the vein by a syringe attached to the tubing. The infusion set is left in place during the test to allow infusion of additional anesthetic as required.

The dog's skin above the jugular vein is then punctured with a standard 14 gauge needle which is then withdrawn. A 15 gauge cannula 20 as shown in FIG. 2 with an internal stylet needle 30 as shown in FIG. 3 is then inserted through the same puncture to prevent damage to the cannula tip 26. The cannula needle 30 is then used to puncture the jugular vein (blood will flow from the needle hub when puncture has occurred). Holding the needle 30 in place, the cannula 20 is slid into the vein and the needle 30 removed. The cannula 20 is then taped to secure it to the dog. It is now ready for insertion of the test sample, which is provided in the form of tubing or a coating on the inner surface of tubing. The tubing has a 1.5 mm. outer diameter and an 0.5 mm. inner diameter.

Each test material tube 10 is pre-marked so that when inserted through the cannula 20 it will protrude about 0.5 cm. passed the tip 26 into the vein. Each tube for testing is inserted into the cannula 20 while infusing 0.9% saline through the tube with a syringe. This prevents the tip of the tube from picking up clots which may form in the cannula 20. After inserting the tube for testing the distal end is lead into a small flask containing corn oil (to inhibit air interface clotting) and the timer started when the first drop of blood appears at the distal end of the tube for testing. When a drop of blood does not fall in one minute from the open end of tube, the timing watch is stopped and the time is recorded as the blood compatibility time. The tube is then removed. Before inserting subsequent tubes for testing of different or the same material, the cannula 20 is washed as follows. The hub 24 of cannula 20 is gripped with the left hand and with a needle 30 attached to a syringe of saline, the needle 30 is inserted through the cannula and blood withdrawn. This is repeated twice to clean the cannula 20. The next tube for testing is then inserted, alternating controls with tubes or catheters of the material to be tested.

When the last tube has been tested, the cannula 20 is removed and pressure applied to the venipuncture until bleeding stops. The dog is rested one week before using again.

The quantitative test to determine the quantity of heparin bound to the surface of a polymeric resin substrate is carried out as follows.

The method is based on the quantitative removal of the dye Azure A by the reactive sites of bound heparin. In the assay, heparinized tubings with known surface area (between 2 and 35 cm$^2$) are exposed to five ml of a 0.001% aqueous solution of Azure A for 45 minutes at 25° C. The quantity of dye removed from the solution is determined by spectrophotometric readings made at 630 nm, with a light path of 1 cm. The dye removed is converted to equivalent amounts of heparin by means of a standard curve prepared by repeating graded amounts of heparin (1–100 micrograms) with five ml of 0.001% Azure A in water, removing the insoluble heparin dye complex by extraction with four ml of cyclohexane, and quantifying the amounts of dye removed spectrophotometrically. The standard curve is then prepared by plotting amount of heparin added versus absorbance at 630 nm. The amount of heparin present on the tubing can then be determined by dividing the amount of heparin removed (derived from the standard curve) by the total surface area of the sample.

The toxicity test results reported were by the method described in the U.S. Pharmacopeia, Vol. XVIII at page 927. In general the method comprises extracting 10 gm or 120 cm$^2$ surface samples of tubing with 20 ml. of cotton seed oil at 70° C. for 24 hours. The extract eluate is injected intraperitoneally in groups of 10 Charles River Mice at a dose of 50 ml eluate per Kg. body weight.

EXAMPLE I

A tube fabricated from 70% by weight polyethylene and 30% by weight bismuth oxychloride is treated by first steeping in an aqueous dispersion of 15% by weight of dodecylmethylammonium chloride for 16 hours at a temperature of 65° C. The steeped tube is then allowed to cool to room temperature, removed from the steeping dispersion and washed with water at a temperature of 25° C. The washed tube is allowed to dry and is then immersed in an aqueous solution of 9% by weight sodium heparinate for 16 hours at 65° C. The heparinized tube is washed in water at a temperature of 25° C. and then cross-linked by immersion in gluteraldehyde for 4 hours at 65° C. The cross-linked tube is then washed with a solution of Triton-100, 5% by weight in water at 25° C. and dried in a vacuum oven at 50° C. for one hour. The dried tube is then washed twice with 70 ml. portions of distilled water and dried again. A representative 10 gm. portion of the tube is then subjected to toxicity testing and a representative length is subjected to blood compatibility testing. The results are shown in Table I, below.

EXAMPLE 2

This example is not an example of the invention but is made for comparative purposes.

The procedure for Example 1, supra is repeated in 3 separate runs, except that the 15% dodecylmethylammonium chloride dispersion as used in Example 1 is replaced with 20%, 12% and 2% dispersions, respectively, of tridodecylmethylammonium chloride. The toxicity and blood compatibility test results are set forth in Table I, below.

EXAMPLE 3

This example is not an example of the invention but is made for comparative purposes.

Repeating the procedure of Example 1, supra, but replacing the 15% dispersion of dodecylmethylammonium chloride as used therein with a 15% dispersion of didodecylmethylammonium chloride, the toxicity and blood compatibility tests reported in Table I, below, are obtained.

TABLE I

| Example No. | Quart. Complex | Conc. | Toxicity (No. of Mice Dead) | Blood Compatibility Minutes |
|---|---|---|---|---|
| 1 | dodecylmethylammonium chloride | 15% | 0 | 186.3 |
| 2 | tridodecylmethylammonium choride | 20% | 5 | 142.0 |
|  | tridodecylmethylammonium chloride | 12% | 2 | 48.0 |
|  | tridodecylmethylammonium chloride | 2% | 0 | 13.5 |
| 3 | didodecylmethylammonium chloride | 15% | 1 | 106.0 |

It will be observed from Table I, above, that, at a desirably effective blood compatibility level, only the tubing of Example 1 provides an acceptable non-toxicity.

EXAMPLE 4

The procedure of Example 1, supra, is repeated except that the polyethylene tubing is used therein is replaced with a polyurethane 0.020″ ID 12 inch length tube. The toxicity and blood compatibility tests are shown in Table II, below.

EXAMPLE 5

This is not an example of the invention, but is provided for comparative purposes.

A representative portion of the polyurethane tubing treated in Example 4, supra, is tested for toxicity and blood compatibility prior to any treatment. The results are shown in Table II, below.

TABLE II

| Example | Toxicity (No. of Mice Killed) | Blood Compatibility (Minutes) |
|---|---|---|
| 4 | 0 | 250.0 |
| 5 (control) | 0 | 19.7 |

EXAMPLE 6

A stainless steel guidewire coated with a 1% solution of polyurethane in tetrahydrofuran and dried is treated with dodecylmethylammonium chloride and heparin following the general procedure set forth in Example 1, supra. The guidewire is then tested for blood compatibility. The test results are set forth in Table III, below.

EXAMPLE 7

As a control, a stainless steel guide wire coated with polyurethane as in Example 6, supra., is tested before treatment with dodecylmethylammonium chloride and heparin, for blood compatibility. The result is shown in Table III, below.

TABLE III

| Example No. | Quart. Complex | Conc. | Clotting Time (Minutes) |
|---|---|---|---|
| 6 | dodecylmethylammonium chloride | 15% | 170.8 |
| 7 | (control) | — | 15.8 |

EXAMPLE 8

Repeating the procedure of Example 1, supra., four times but in each case using a tube fabricated from a material different than the polyethylene/bismuth composition used therein, there is obtained an article of reduced thrombogenicity and toxicity.

The toxicity and blood compatibility test results are shown in Table IV, below, with the identity of the polymer material.

TABLE IV

| Tubing Material | Toxicity (No. of Mice Dead) | Blood Compatibility Minutes | |
|---|---|---|---|
| | | Before Treatment | After Treatment |
| Silicone rubber | 0 | 17 | 62+ |
| Polyvinyl chloride | 0 | 14.7 | 170+ |
| Polyurethane | 0 | 19.7 | 210+ |
| Polytetrafuloroethylene | 0 | 10.0 | 70+ |
| Nylon −6 | 0 | — | — |
| Polycarbonate | 0 | — | — |
| Polyoxymethylene | 0 | — | — |
| Polypropylene | 0 | — | — |
| Polystyrene | 0 | — | — |

EXAMPLE 9

The procedure of Example 1, supra., is repeated four times on the polyurethane tubing, except that in three repetitions, the 9% by weight aqueous dispersion of heparinate as used therein is replaced with 2%, 5% and 20% by weight dispersions of the chloride. The product tubings are subjected to physical testing. The blood compatibility test results and the quantity of heparin attached to the article surface is shown in Table V, below, with the concentration of heparin used in the preparation.

TABLE V

| Percent Heparin | Weight of Heparin Attached ($\mu g/cm^2$) | Blood Compatibility (Minutes) |
|---|---|---|
| 2 | 0.49 | 112 |
| 5 | 2.34 | 172 |
| 9 | 10.85 | 221 |
| 20 | 18.08 | 521 |

It will be seen from the Example 9 that when the concentration of heparin is from 5 to 20 percent, the weight of heparin attached is substantially increased as are the compatibility times.

EXAMPLE 10

The procedure of Example 4, supra., is repeated five times, except that in each case the dodecylmethylammonium chloride is used therein is replaced with one of the following:

(A) a 15% aqueous dispersion of decylmethylammonium chloride (B) a 15% aqueous dispersion of tetradecylmethylammonium chloride (C) a 10% aqueous dispersion of hexadecylmethylammonium chloride (D) an 8% aqueous dispersion of octadecylmethylammonium chloride (E) an 8% ethanol dispersion of dodecylhexylammonium chloride Representative portions of the tubing obtained are tested for their toxicity and blood compatibility. The test results are set forth in Table VI below.

TABLE VI

| Quart. Complex | Toxicity (No. of Mice Dead) | Blood Compatibility (Minutes) |
|---|---|---|
| decylmethylammonium chloride (control) | 0 | 14.1 |
| tetradecylmethylammonium chloride | 0 | 175.0 |
| hexadecylmethylammonium chloride | 0 | 186.0 |
| octadecylmethylammonium chloride | 0 | 153.0 |
| dodecylhexylammonium chloride | 0 | 180.0 |

The untreated tubing, when tested for blood compatibility as a control showed 14.9 minutes.

It will be observed from the Example 10 that with the exception of the control run, the treated resin materials showed both an acceptable blood compatibility and freedom from toxicity.

What is claimed is:

1. An article for use in association with whole blood, which comprises;

a solid, polymeric resin substrate; and a compound of the formula:

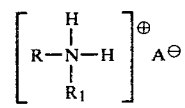

wherein R is alkyl of 12 to 18 carbon atoms, inclusive, $R_1$ is lower alkyl and A represents the negative ion of a salt of heparin, affixed to said substrate.

2. The article of claim 1 wherein said resin comprises polyethylene.

3. The article of claim 1 wherein said resin is polyurethane.

4. The article of claim 1 wherein said resin is polytetrafluoroethylene.

5. The article of claim 1 wherein the proportion of heparin affixed to the substrate is at least 2.0 $\mu g/cm^2$ of resin substrate surface.

6. The article of claim 1 wherein the resin is selected from the group consisting of polyethylene, polyacrylics, polypropylene, polyvinyl chloride, polyamides, polyurethanes, polyvinylpyrrolidone, polyvinyl alcohols, polyoxymethylene cellulose acetate, polystyrene, polytetrafluoroethylene, polyesters, silicone rubber, natural rubber and polycarbonates.

7. An article for use in association with whole blood, which comprises;

a solid polymeric resin substrate; and
a compound of the formula:

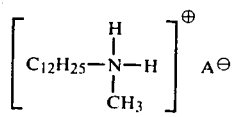

wherein A represents the residue of sodium heparin after removal of the sodium ion, affixed to said substrate.

8. A method of improving the blood compatibility of a solid polymeric resin which comprises affixing thereto a compound of the formula:

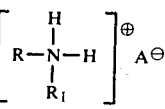

wherein R is alkyl of 12 to 18 carbon atoms, inclusive, $R_1$ is lower alkyl and A represents the negative ion of a salt of heparin.

9. The method of claim 8 wherein the compound is selected from the group consisting of dodecylmethylammonium chloride, tetradecylmethylammonium chloride, hexadecylmethylammonium chloride, octadecylmethylammonium chloride and dodecylhexylammonium chloride.

* * * * *